US007431928B2

(12) United States Patent
Cardinaud et al.

(10) Patent No.: US 7,431,928 B2
(45) Date of Patent: Oct. 7, 2008

(54) IDENTIFICATION OF NEW CD8 EPITOPES FROM HIV-1 PROTEINS

(75) Inventors: Sylvain Cardinaud, Carrière-sur-Seine (FR); André Habel, Paris (DE); Pierre Langlade-Demoyen, Paris (FR); François Lemonnier, Bourg-la-Reine (FR)

(73) Assignees: Institut Pasteur, Paris (FR); Institut National de la Sante et de la Recherche, Paris (FR)

( * ) Notice: Subject to any disclaimer, the term of this patent is extended or adjusted under 35 U.S.C. 154(b) by 0 days.

(21) Appl. No.: 11/339,605

(22) Filed: Jan. 26, 2006

(65) Prior Publication Data
US 2006/0115488 A1 Jun. 1, 2006

Related U.S. Application Data

(63) Continuation of application No. 10/491,008, filed as application No. PCT/IB02/04576 on Sep. 27, 2002, now Pat. No. 7,022,325.

(30) Foreign Application Priority Data
Sep. 28, 2001 (CA) .................................. 2357906

(51) Int. Cl.
*A61K 39/00* (2006.01)
*A61K 39/12* (2006.01)
*A61K 39/21* (2006.01)
*A61K 39/385* (2006.01)
*C12Q 1/70* (2006.01)
*G01N 33/53* (2006.01)
*G01N 33/567* (2006.01)
*G01N 33/00* (2006.01)

(52) U.S. Cl. ............... 424/188.1; 424/184.1; 424/185.1; 424/186.1; 424/187.1; 424/193.1; 530/300; 435/5; 435/7.2; 435/7.21; 435/7.24

(58) Field of Classification Search .............. 424/184.1, 424/185.1, 186.1, 187.1, 188.1; 530/350, 530/826
See application file for complete search history.

(56) References Cited

U.S. PATENT DOCUMENTS 5,459,060 A * 10/1995 Cotropia ................... 435/339.1
6,268,484 B1 * 7/2001 Katinger et al. ........ 530/388.35

FOREIGN PATENT DOCUMENTS

| WO | WO 9744667 A2 * | 11/1997 |
| WO | WO 99/45954 | 9/1999 |
| WO | WO 99/58658 | 11/1999 |
| WO | WO 01/24810 A1 | 4/2001 |
| WO | WO 02/20035 A1 | 3/2002 |

OTHER PUBLICATIONS

Altman et al. HIV escape: there and back again. Nature Medicine Mar. 2004, vol. 10, No. 3, pp. 229-230.*
Friedrich et al. Reversion of CTL escape—variant immunodeficiency viruses in vivo. Nature Medicine Mar. 2004, vol. 10, No. 3, pp. 275-281.*
Leslie et al. HIV evolution: CTL escape mutation and reversion after transmission. Nature Medicine Mar. 2004, vol. 10, No. 3, pp. 282-289.*
Desrosiers. Prospects for an AIDS vaccine. Nature Medicine Mar. 2004, vol. 10, No. 3, pp. 221-223.*
Letvin. Progress toward an HIV vaccine, Annual Review of Medicine 2005, vol. 56, pp. 213-223.*
Altfeld et al. Vpr Is Preferentially Targeted by CTL During HIV-1 Infection. The Journal of Immunology, Sep. 1, 2001, vol. 167, p. 2743-2752.*
Altman et al. Phenotypic Analysis of Antigen-Specific T lymphocytes. Science Oct. 4, 1996, vol. 274, p. 94-96.*
Altman et al. MHC Tetramer Analyses of CD8+ T Cell Responses to HIV and SIV. HIV Databases Review Artivle 1998 [online], Los Alamos National Laboratory, United States [retrieved on Jun. 26, 2007]. Retrieved from the Internet <URL: www.hiv.lanl.gov/content/hiv-dab/REVIEWS/articles/Safrit.html>.*
Kusk et al. Mapping of a New Immunodominant Human Linear B-cell Epitope on the Vpu protein of the HIV-1 1993. Journal of Acquired Immune Deficiency Syndromes vol. 6. pp. 334-338.
Jin, X. et al., "Identification of Subdominant Cytotoxic T Lymphocyte Epitopes Encoded by Autologous HIV Type 1 Sequences, Using Dendritic Cell Stimulation and Computer-Driven Algorithm", Aids Research and Human Retroviruses, vol. 16, pp. 67-76, (Nov. 1, 2000).
Los Alamos National Laboratory, HIV Database, Immunology Database, 'Online!—Dec. 2000, Retrieved from the Internet: url:http://hiv-web.lanl.gov/content/hiv-db/immunology/PDF/2000/2/alignments/p2p7p1p6.pdf, Retrieved on Jul. 14, 2003!
Aids Vaccine 2001, Posters Conference 2001, 'Online!—Sep. 8, 2001, XP-002247713, Retrieved from the Internet: URL:http://www.aidsvaccine2001.org/Posters/305.pdf, Retrieved on Jul. 15, 2003!
Kuroda et al., "Analysis of Gag-Specific Cytotoxic T Lymphocytes in Simian Immunodeficiency Virus-Infected Rhesus Monkeys by Cell Staining with a Tetrameric Major Histocompatibility Complex Class I-Peptide Complex," *J. Exp. Med.*, vol. 187, No. 9, May 4, 1998, p. 1373-1381.

* cited by examiner

*Primary Examiner*—Bruce Campell
*Assistant Examiner*—Louise Humphrey
(74) *Attorney, Agent, or Firm*—Finnegan, Henderson, Farabow, Garrett & Dunner, L.L.P.

(57) ABSTRACT

The invention relates to the identification and the selection of CTL epitopes able to induce a protection against an HIV infection. More particularly, the invention is concerned with peptides and nucleic acid sequence coding for these peptides derived from HIV-1 proteins such as GAG, POL, ENV, VIF, TAT, VPU, REV and their applications. Preferably the immunogenic peptides are selected from the group consisting of SEQ ID NOs:1 to 18 and functional derivatives thereof. The invention also relates to antibodies directed against said peptides.

7 Claims, 6 Drawing Sheets

US 7,431,928 B2

IDENTIFICATION OF NEW CD8 EPITOPES FROM HIV-1 PROTEINS

CROSS REFERENCE TO RELATED APPLICATION

This is a continuation of application Ser. No. 10/491,008, filed Oct. 12, 2004, which issued as U.S. Pat. No. 7,022,325 on Apr. 4, 2006, and which is a 35 U.S.C. § 371 national stage filing of International Application PCT/IB02/04576, filed Sep. 27, 2002, which claims benefit of priority of Canadian Application No. 2,357,906, filed Sep. 28, 2001, all of which are incorporated herein by reference.

The present invention relates to the identification and the selection of CTL epitopes able to induce a protection against an HIV infection. More particularly, the invention is concerned with peptides and nucleic acid sequences coding for these peptides derived from HIV-1 proteins such as GAG, POL, ENV, VIF, TAT, VPU, REV.

Many scientific publications disclosed HIV epitopes having the property to induce in animals a B cell response as well as a T-cell response specific for HIV. The importance of CTL response under HIV control have been demonstrated in many experiences. Indeed, it is known that there is an inverse correlation between CTL response and HIV viremia in patients; that CD8 (CTL) depletion in monkeys leads to an increase of the viremia; that there are subjects who are continually exposed to the virus but are not infected and who possess a strong CTL response and that specific HIV CTL clones have been shown to inhibit the viral replication in vitro.

Although that numerous HIV-1 proteins are known and under study (see WO 01/27291; Altfeld M. et al. (2001), *The Journal of Immunology*, 167: 2743-2752; and Jin X., et al. (2000), *AIDS research and Human retroviruses*, 16: 67-76), the extent to which these proteins are targeted in natural infection, as well as precise CTL epitopes within them, remain to be defined.

Therefore, there is a strong need for peptides and epitopes that are capable to induce in animals a B cell response, as well as a T cell response, against HIV-1 proteins, and to the use of such peptides and epitopes in the diagnostic, in the prevention/protection against an HIV infection and in the treatment of HIV.

The present invention fulfils these needs and also other needs which will be apparent to those skilled in the art upon reading the following specification.

The present invention relates to the identification and the selection of CTL epitopes able to induce a protection against an HIV infection. More particularly, the invention is concerned with peptides and nucleic acid sequences coding for these peptides derived from HIV-1 proteins such as GAG, POL, ENV, VIF, TAT, VPU, REV.

More particularly, the invention provides new immunogenic peptides and epitopes capable of inducing a cytotoxic CD8 T-lymphocytes (CTLs) as large as possible.

The invention also provides antibodies binding to the immunogenic peptides of the invention thereto.

The invention further relates to pharmaceutical compositions and to methods for inducing/stimulating of an immune response into a subject.

An advantage of the present invention is that it identifies, among HIV-1 proteins, epitopes capable of inducing a specific cytotoxic CD8 T-lymphocytes (CTLs) response. The invention also provides new HIV CTL epitopes leading in the increase of the breadth of the HIV/CTL response after vaccination.

Other objects and advantages of the present invention will be apparent upon reading the following non-restrictive detailed description, made with reference to the accompanying drawings.

A) DEFINITIONS

Figure 1:
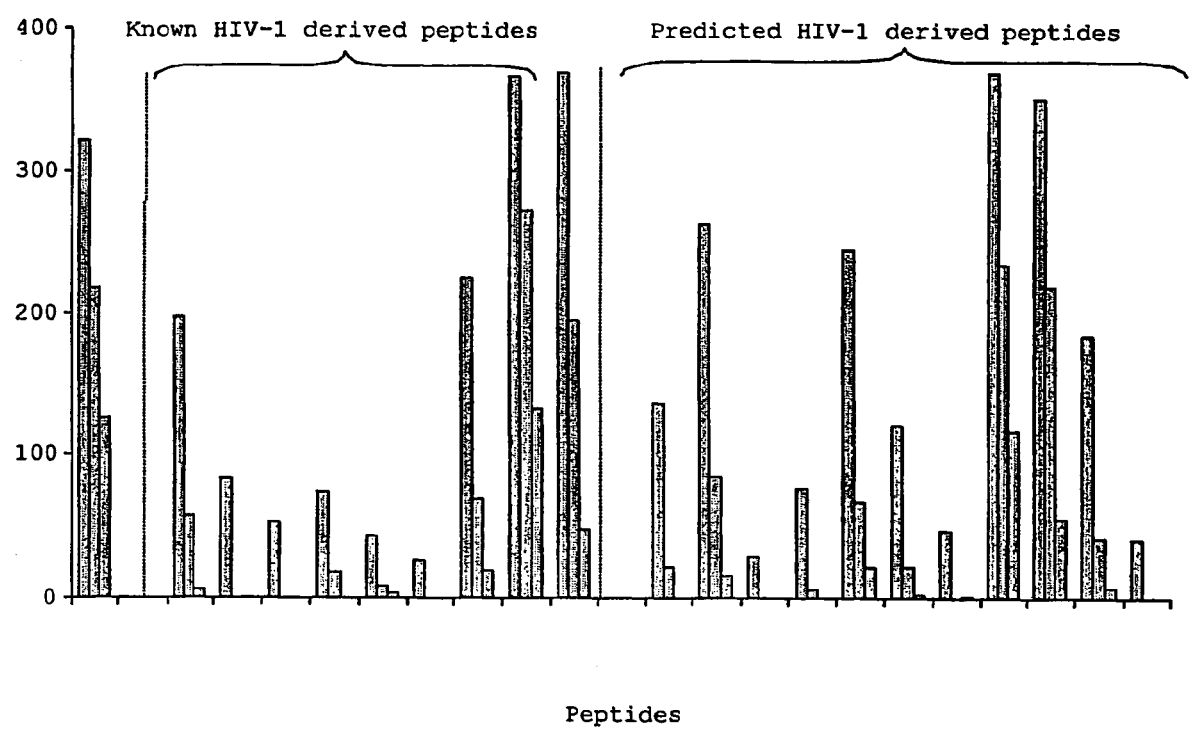
FIG. 1 is a graph showing the pattern for IFNγ ELISPOT responses against HIV-1 derived epitopic peptides (known and new "coding" peptides) of one patient (BNC).

In order to provide an even clearer and more consistent understanding of the specification and the claims, including the scope given herein to such terms, the following definitions are provided:

Allelic variant: refers to a peptide having from one to two amino acid substitutions from a parent peptide, but retaining the binding specificity and/or physiological activity of the parent peptide. As used herein, "retaining the binding specificity of the parent peptide" means being able to bind to a monoclonal or polyclonal antibody that binds to one of the peptides with an affinity that is at least one-tenth, more preferably at least one-half, and most preferably at least as great as that of one of the actual peptides. Determination of such affinity is preferably conducted under standard competitive binding immunoassay conditions. "Retaining the physiological activity of the parent peptide" means retaining the ability of any one of the peptides shown in SEQ ID NOs 1 to 18. The term "allelic variants" is specifically intended to include any human analogs of the peptides set forth in SEQ ID NOS. 1 to 18, which do not have the identical amino acid sequence thereof.

Antibody: refers to a glycoprotein produced by lymphoid cells in response to a stimulation with an immunogen. Antibodies possess the ability to react in vitro and in vivo specifically and selectively with an antigenic determinant or epitope eliciting their production or with an antigenic determinant closely related to the homologous antigen As used herein, a protein/peptide is said to be a "chemical derivative" of another protein/peptide when it contains additional chemical moieties not normally part of the protein/peptide, said moieties being added by using techniques well known in the art. Such moieties may improve the protein/peptide solubility, absorption, bioavailability, biological half life, and the like. Any undesirable toxicity and side-effects of the protein/peptide may be attenuated and even eliminated by using such moieties. For example, proteins/peptides can be covalently coupled to biocompatible polymers (polyvinyl-alcohol, polyethylene-glycol, etc) in order to improve stability or to decrease/increase their antigenicity.

Derived: A protein/peptide is said to "derive" from a protein/peptide/gene or from a fragment thereof when such protein/peptide/gene comprises at least one portion, substantially similar in its sequence, to the native protein/peptide/gene or to a fragment thereof.

Fragment: refers to a section of a molecule, such as protein/peptide or nucleic acid, and is meant to refer to any portion of the amino acid or nucleotide sequence.

A "functional derivative", as is generally understood and used herein, refers to a protein/peptide sequence that possesses a functional biological activity that is substantially similar to the biological activity of the whole protein/peptide sequence. A functional derivative of a protein/peptide may or may not contain post-translational modifications such as covalently linked carbohydrate, if such modification is not necessary for the performance of a specific function. The term "functional derivative" is intended to the "fragments", "segments", "variants", "allelic variants", "analogs" or "chemical derivatives" of a protein/peptide.

Fusion protein: A protein formed by the expression of a hybrid gene made by combining two gene sequences. Typically, this is accomplished by cloning a cDNA into an expression vector in frame with an existing gene.

Immunogenic: Refers to the property of a molecule or compound, such as a protein/peptide/nucleic acid to induce in vivo or in vitro a cellular or humoral immune response.

Immune response: Refers to an in vivo or in vitro reaction in response to a challenge by an immunogen. An immune response is generally expressed by an antibody production and/or a cell-mediated immunity or immunologic tolerance.

Isolated or Purified: Means altered "by the hand of man" from its natural state, i.e., if it occurs in nature, it has been changed or removed from its original environment, or both. For example, a polynucleotide naturally present in a living organism is not "isolated", the same polynucleotide separated from the coexisting materials of its natural state, obtained by cloning, amplification and/or chemical synthesis is "isolated" as the term is employed herein. Moreover, a polynucleotide that is introduced into an organism by transformation, genetic manipulation or by any other recombinant method is "isolated" even if it is still present in said organism.

Oligonucleotide or Polynucleotide means nucleic acid, either desoxyribonucleic acid (DNA), or ribonucleic acid (RNA), in single-stranded or double-stranded form or molecule having one nucleotide or more, whether occurring naturally or non-naturally in a particular cell, tissue or organism, and any chemical modifications thereof. Such modifications include, but are not limited to providing other chemical groups that incorporate additional charge, polarizability, hydrogen bonding or electrostatic interaction to one or more of nucleic acid bases of the oligonucleotide. Examples of Modifications are, but are not limited to, modifying the bases such as substitution of 5-bromouracil, 5-position pyrimidine modifications, 8-position purine modifications, modifications at cytosine exocyclic amines, 2'-position sugar modifications, methylations, unusual base-pairing combinations such as the isobases isocytidine and isoguanidine, backbone modifications, 3' and 5' modifications such as capping, and the like. Are also compatible with the current invention, modifications that occur after each round of amplification in a reversible or irreversible manner.

Peptide: includes any natural or synthetic compounds containing two or more amino acids connected to each other in a linear array by peptides bonds. Such linear array may optionally be cyclic, i.e., the ends of the linear peptide or the side chains of amino acids within the peptide may be joined, e.g., by a chemical bond. The peptides according to the invention may include from about three to about 500 amino acids, and may further include secondary, tertiary or quaternary structures, as well as intermolecular associations with other peptides or other non-peptide molecules. Such intermolecular associations may be through, without limitation, covalent bonding (e.g., through disulfide linkages), or through chelation, electrostatic interactions, hydrophobic interactions, hydrogen bonding, ion-dipole interactions, dipole-dipole interactions, or any combination of the above. This term also includes proteins and fragments thereof produced through recombinant means, and/or that has been associated or not with other peptides coding for tumoral, viral, bacterial or fungic epitopes for forming a fusion protein.

Specific lysis: in the enclosed example, specific lysis means that at least 10% of the HIV infected cells are killed within 4 hours.

Vaccine: a preparation of antigenic material comprising at least one peptide according to the invention and/or at least one polynucleotide coding the same, that can be used to stimulate a specific immune response able to confer a protection against HIV or limit an HIV infection.

The term "variant" as is generally understood and used herein, refers to a protein that is substantially similar in structure and biological activity to either the protein or fragment thereof. Thus two proteins are considered variants if they possess a common activity and may substitute each other, even if the amino acid sequence, the secondary, tertiary, or quaternary structure of one of the proteins is not identical to that found in the other.

Vector: A self-replicating RNA or DNA molecule which can be used to transfer an RNA or DNA segment from one organism to another. Vectors are particularly useful for manipulating genetic constructs and different vectors may have properties particularly appropriate to express protein(s) in a recipient during cloning procedures and may comprise different selectable markers. Bacterial plasmids are commonly used vectors.

B) GENERAL OVERVIEW OF THE INVENTION

The present invention relates to derived peptides from HIV-1 proteins, and more particularly from the GAG, POL, ENV, VIF, TAT, VPU, REV proteins of HIV-1. The invention also relates to nucleic acid sequences coding for said peptides. The peptides and the nucleic acids of the invention may be useful for the prevention and/or treatment of HIV-1 infections.

The peptides of the invention may also be used for detecting an early CTL response against of HIV-1, for priming in vitro immune cells of a eukaryotic subject, for stimulating a subject immune response, and stimulating ex vivo or in vivo a human immune response against HIV-1.

The peptides/nucleic acids of the present invention may be used in all members of the class Vertebrates. Preferably, the vertebrate is a mammalian subject including, without limitation, human and non-human primates, farm animals, domestic animals, laboratory animals.

C) IMMUNOGENIC PEPTIDES AND CORRESPONDING NUCLEOTIDES

In one aspect, the invention is directed to immunogenic peptides that derive from the HIV-1 antigen. Advantageously, the peptides of the invention are capable of inducing an in vitro, ex vivo and/or in vivo CTL response against HIV-1 in a mammal.

More particularly, the immunogenic peptides according to the invention can induce in vitro, ex vivo and/or in vivo specific cytotoxic CD8 T-lymphocytes (CTLs) capable of eliminating specifically HIV-1 infected cells. Preferably, the immunogenic peptides comprise between 9 and 30 amino acid having at least 60% homology with any one of the peptide of SEQ ID NOs 1 to 18. More preferably, the peptides of the invention are nonameric or docameric peptides and even more preferably, they are selected from the group consisting of SEQ ID NOs:1 to 18 and even more those particularly selected from the group consisting of SEQ ID Nos: 1, 2, 3, 6 and 15 (see Tables 1 and 2 hereafter). However the present invention is not restricted to these specific peptides by it encompasses also "functional derivatives" thereof, including "fragments", "variants", "allelic variants", "analogs" or "chemical derivatives" of these peptides, having a comparable specificity and/or biological activity as the peptides of SEQ ID NOs:1 to 18.

Modified peptides within the scope of the present invention include those in which one or more amide bond is replaced by a non-amide bond, and/or one or more amino acid side chain is replaced by a different chemical moiety, or one or more of the N-terminus, the C-terminus, or one or more side chain is protected by a protecting group, and double bonds and/or cyclization and/or stereospecificity is introduced into the amino acid chain to increase rigidity, and/or binding affinity and/or enhance resistance to enzymatic degradation, of the peptides of SEQ ID NOs:1 to 18. Since all the variations are known in the art, a person skilled in the art will be able to produce, test, identify and select other peptides/epitopes according to the present invention (see e.g. Horwell et al, Bioorg. Med. Chem. 4: 1573 (1976); Liskamp et al., Recl. Trav. Chim. Pays-Bas 1:113 (1994); Gante et al, Angew. Chem. Int. Ed. Engl. 33:1699 (1994); and Seebach et al, Helv. Chim. Acta 49:313 (1996)).

For instance, it is possible to substitute amino acids by equivalent amino acids. "Equivalent amino acid" is used herein to name any amino acid that may substituted for one of the amino acids belonging to the initial peptide structure without modifying the hydrophilicity properties and the biological target of the initial peptide structure. Preferably, the peptides containing one or several "equivalent" amino acids retain their specificity and affinity properties to the biological targets of the peptide according to the invention. In other words, the "equivalent" amino acids are those which allow the generation or the preparation of a polypeptide or peptide with a modified sequence as regards to the peptides according to the invention, said modified polypeptide or peptide being able to act as an agonist or an antagonist molecule of the peptide according to the invention. These equivalent amino acids may be determined by their structural homology with the initial amino acids to be replaced and by their biological activity on the target cells of the peptides according to the invention. As an illustrative example, it should be mentioned the possibility of carrying out substitutions like, for example, leucine by valine or isoleucine, aspartic acid by glutamic acid, glutamine by asparagine, asparagine by lysine etc., it being understood that the reverse substitutions are permitted in the same conditions. In some cases, it may also be possible to replace a residue in the L-form by a residue in the D-form or the replacement of the glutamine (Q) residue by a Pyroglutamic acid compound. The synthesis of peptides containing at least one residue in the D-form is, for example, described by KOCH et al. (1977).

Tables 1 and 2 show the amino acid sequence of the preferred peptides of the invention (SEQ ID NOs:1-18) and, for each of these peptides, the corresponding nucleotide sequence encoding these peptides (SEQ ID NOs:19-36; Table 2). However, since the genetic code is degenerated, it is clear that the nucleotide sequences given in Table 2 are, for each of these peptides, one specific example of the many possible examples of sequence for coding these peptides. A person skilled in the art will easily be capable of determining other nucleotide sequences coding for the peptides of the present invention.

The peptides of the present invention may be prepared by any suitable process. Preferably, they are obtained by chemical synthesis in liquid or solid phase by successive couplings of the different amino acid residues to be incorporated (from the N-terminal end to the C-terminal end in liquid phase, or from the C-terminal end to the N-terminal end in solid phase) wherein the N-terminal ends and the reactive side chains are previously blocked by conventional groups. For solid phase synthesis the technique described by Merrifield (J. Am. Chem. Soc., 85:2149-2154) may be used. Alternatively, the technique described by Houbenweyl in 1974 may also be used.

Typically, in order to produce a peptide chain using the Merrifield process, a highly porous resin polymer is used, on which the first C-terminal amino acid of the chain is fixed. This amino acid is fixed to the resin by means of its carboxyl group and its amine function is protected, for example, by the t-butyloxycarbonyl group. When the first C-terminal amino acid is thus fixed to the resin, the protective group is removed from the amine function by washing the resin with an acid. If the protective group for the amine function is the t-butyloxycarbonyl group, it may be eliminated by treating the resin with trifluoroacetic acid. The second amino acid which supplies the second residue of the desired sequence is then coupled to the deprotected amine function of the first C-terminal amino acid fixed to the chain. Preferably, the carboxyl function of this second amino acid is activated, for example, using dicyclo-hexylcarbodiimide, and the amine function is protected, for example, using t-butyloxycarbonyl. In this way, the first part of the desired peptide chain is obtained, which comprises two amino acids, the terminal amine function of which is protected. As before, the amine function is deprotected and the third residue can then be fixed, under similar conditions, to those used in the addition of the second C-terminal amino acid. Thus, the amino acids which are to form the peptide chain are fixed, one after another, to the amine group, which is previously deprotected each time, to the portion of the peptide chain already formed, which is attached to the resin. When all the desired peptide chain is formed, the protecting groups are eliminated from the various amino acids which constitute the peptide chain and the peptide is detached from the resin, for example using hydrofluoric acid.

The peptides of the present invention may also be obtained by biological or genetic engineering processes. A typical example comprises the use of expression vectors comprising a polynucleotide sequence coding for the peptide of interest (such vectors are within the scope of the present invention). Multimer of each peptide can also be produced by genetic engineering technology by expressing of a polynucleotide coding for multiple copies of a monomer, or coding for different monomers.

The peptides of the present invention may also be incorporated in polypeptides having a length varying from about 10 to about 50 amino acids, preferably about 15 amino acids. According to a preferred embodiment, the peptides are incorporated in a tetrameric complex of HLA-A0201 or HLA-B0702 comprising a plurality of identical or different peptides/polypeptides according to the invention. According to another preferred embodiment, the peptides of the invention are incorporated into a support comprising at least two peptide molecules. Examples of suitable support include polymers, lipidic vesicles, microspheres, latex beads, polystyrene beads, proteins and the like.

In another aspect, the invention is directed to a method for producing, in vitro, an immunogenic peptide, comprising: culturing in vitro, in a suitable culture medium, a cell incorporating an expression vector as described previously; and collecting in the culture medium immunogenic peptides produced by these cells. Therefore, the invention is also concerned with cells, such as recombinant bacteria, transformed or transfected by a virus or plasmid for expressing the peptides of the invention. Methods for producing such cells and methods for using these cells in the production of proteins/peptides are well known in the art and will no be described in detail herein.

The peptides, polypeptides and polynucleotides of the invention may also be used for producing polyclonal or monoclonal antibodies capable of recognizing and binding the same. Methods for producing such antibodies are well known in the art. These antibodies may be used for the preparation of a medicine for the prevention or treatment of human HIV-1 infections.

D) PHARMACEUTICAL COMPOSITIONS

The peptides/polypeptides of the present invention, the polynucleotides coding the same, and polyclonal or monoclonal antibodies produced according to the invention, may be used in many ways as antitumoral agents, for the preparation of pharmaceutical compositions, for the preparation of an antitumoral vaccine, for the treatment or the prevention of HIV infections.

Therefore, in another aspect, the invention is directed to pharmaceutical compositions comprising:

a) at least one component selected from the group consisting of:
  an immunogenic peptide/polypeptide and/or a polynucleotide and/or a fragment thereof and/or an antibody as defined previously; and
  specific CD8 T-cells primed against an immunogenic peptide/polypeptide and/or a fragment thereof; and b) a pharmaceutically acceptable vehicle or carrier.

According to a preferred embodiment, the composition further comprises at least one CD4 peptide. More preferably, the CD4 peptide is linked to the HIV CD8 epitope. Even more preferably, the CD4 peptide is an HIV CD4 epitope.

The compositions of the invention may be in a solid or liquid form or in any suitable form for a therapeutic use. They may be formulated for a rapid or slow release of its components and may further comprise compounds for stimulating/inhibiting the immune system. The compositions of the invention may be prepared according to conventional methods known in the art.

E) STIMULATION OF A IMMUNE RESPONSE

In another aspect, the invention is directed to a method for priming human CD8 cells in vitro, comprising the steps of:

a) isolating HLA-B0702 lymphoid or myeloid cells from human subject; and b) loading in vitro the cells isolated at step a) with at least one immunogenic peptide/polypeptide and/or polynucleotide as defined previously.

According to a preferred embodiment, the method further comprises the steps of:

c) isolating CD8+ T-cells from the subject; and d) using the cells primed at step b) for priming in vitro the CD8+ T-cells isolated at step c).

In a further aspect, the invention is directed to a method for stimulating a subject immune response comprising:
  administering into a compatible subject HLA-B0702 lymphoid or myeloid cells primed in vitro using the method defined hereinabove; and/or
  administering into a compatible subject CD8+ T-cells primed according to the method using the method defined hereinabove.

The invention also provides an ex vivo stimulation method of the human immune response. This method comprises the steps of isolating from a human autologous lymphoid or myeloid cells; incubating these isolated cells in vitro with at least one immunogenic peptide/polypeptide and or a polynucleotide as defined previously, these cells allowing the induction of a cytotoxic response in vitro. In a related aspect, the invention provides a method for stimulating in vivo a human immune response against HIV-1, the method comprising administering to a HLA-B0702 patient in need thereof either cytotoxic cells, lymphoid or myeloid cells treated in vitro according to the ex vivo stimulation process of the invention.

In another aspect, the invention is directed to a method for detecting an early CTL response against HIV-1. This method comprises the steps of:
  providing a tetrameric complex of HLA-B0702 comprising at least one immunogenic peptide according to the invention;
  incubating this complex with peripheral blood lymphocytes of a subject; and
  determining the presence of HIV-1 specific CTL.

The presence of HIV-1 specific CTL may be done by comparing cells from the subject with normal cells in culture using any suitable method such as FACS.

In another aspect, the invention is directed to a method for stimulating a human immune response against HIV-1, comprising:
  isolating from a human HIV-1 specific CTLs;
  amplifying ex vivo the isolated HIV-1 specific CTLs; and
  injecting in a compatible human in need thereof, the HIV-1 specific CTLS.

The following examples are illustrative of the wide range of applicability of the present invention and is not intended to limit its scope. Modifications and variations can be made therein Without departing from the spirit and scope of the invention. Although any methods and: materials similar or equivalent to those described herein can be used in the practice for testing of the present invention, the preferred methods and materials are described.

EXAMPLE 1

Materials and Methods

HLA-B7B7 $K^d$ Chimerical Transgene and Animals.

The HLA-B*0702 gene was isolated from a cosmid library from the HLA-B*0702 homozygous HHK lymphoblastoid human; cell line. A 1.5 Kb EcoRI-Kpn I fragment (promoter, exons 1 to 3) of the HLA-B*0702 gene was ligated to a 4.1 Kb Kpn I-Hind III fragment (exons 4 to 8) of the H-2 $K^d$ gene. The chimerical HLA-B7B7$K^d$ gene was micro-injected as an EcoRI-Hind III fragment in C57BL/6×SJL oocytes. Transgenic animals were backcrossed (×12) on C57BL/6 JICO(H-$2^b$) mice, before derivation of animals homozygous for the transgene. These mice were subsequently intercrossed with H-2 $K^{bo}$ $D^{bo}$ double KO mice (backcrossed 6 times on C57BL/6 JICO, (7, 11) to derive HLA-B7B7K, H-2 $K^{bo}$ $D^{bo}$ double KO homozygous mice (backcrossed 6 times on C57BL/6 JICO). Mice were bred in our animal facility and used for experimentation between 6 and 10 weeks of age.

Peptide Binding

Peptides, purchased from SYNT:EM (Nimes, France), were dissolved in DMSO (1 mg of peptide/20 μl) and subsequently diluted in PBS (2 mg/ml). Peptides and HLA-B*0702 transfected TAP-T2 (7) cells were incubated overnight at 37° C. (1×10$^6$ cells/ml) in FCS-free medium supplemented with 100 ng/ml of human 12-microgbulin (SIGMA, St Louis, Mo.) in the absence (negative control) or presence of either reference human cytomegalovirus (CMV) pp65-265-274 (RPHERNGFTV, R10V, SEQ ID NO: 50) or tested peptides at various final concentrations (100, 10, 1 and 0.1 μM). Following a 1 h incubation with Brefeldin A (0.5 μg/ml, SIGMA), T2-B*0702 cells were labelled (30 min, 4° C.) with saturating concentration of ME.1 anti-HLA-B07 mAb, then washed twice and finally stained with FITC-conjugated F(ab)'2 goat anti-mouse Ig, before FACS analysis. For each peptide, the concentration needed to reach 20% of the maximal fluorescence (as defined with the R10V peptide) was calculated. Relative affinity is the ratio of the concentrations of the tested and R10V reference peptide needed to reach this value: the lower the relative affinity, the stronger the binding.

Induction of CTL and Cytolytic Assays

For peptide immunisations, groups of 6 mice were injected s.c. at the base of the tail with 50 μg of HLA-B0702-restricted peptide and 140 μg of the Ia$^b$-restricted helper peptide (hepatitis B virus core 128-140, TPPAYRPPNAPIL, T13L, SEQ ID NO: 51) (8) co-emulsified in 100 μl of incomplete Freund adjuvant (IFA, Difco, Detroit, Mich.). Eight days later, spleen cells were re-stimulated in vitro as described before with peptide-loaded, LPS-induced syngeneic lymphoblasts (9). On day 6, cultured cells were tested in a 4 h $^{51}$Cr-release assay, using experimental or control human CMV pp65-265-274 R10V peptide-pulsed, $^{51}$Cr-labeled HLA-B7B7 K$^d$-P815 cells. Specific lysis was calculated as follow: (experimental–spontaneous release)/(total–spontaneous release)×100 subtracting the background lysis of R10V control-peptide-loaded target cells. Mice were considered as responder when specific lysis ≧10% was observed.

Immunofluorescence Assays.

Red cell-depleted, nylon-wool purified spleen T lymphocytes were analyzed for MHC class I molecule expression in an indirect immunofluorescence assay. First layer mAb (B8-24-3 anti-H-2 K$^b$, B 22.249.R19 anti-H-2 D$^b$, and ME.1 anti-HLA-B0702) were incubated at saturating concentrations (30 min, 4° C.) with cells. After 3 washes, mAb fixation was revealed with FITC-conjugated F(ab)'2 goat anti-mouse Ig (Caltag, San Francisco, Calif.), and cells were FACS-analyzed (FACS Calibur, Beckton Dickinson, San Jose, Calif.). Percentages of CD4$^+$ and CD8$^+$ splenic T lymphocytes were determined by double staining using FITC-conjugated rat anti-mouse CD4 (RM4-5) and phycoerythrin-conjugated rat anti-mouse CD8-β (CT-CD8b) mAb (Caltag). Expression of the different T cell receptor (TCR) Vβ chains was similarly analyzed using purified Vβ2 (B.20.6), Vβ4 (KT.10.4), Vβ5.1,.2 (MR.9.4), Vβ6 (44.22.1), Vβ7 (TR.130), Vβ8.1,.2,.3 (F.23.1), Vβ9 (MR.10.2) Vβ10 (B.21.5), Vβ11 (RR.3.15), Vβ12 (MR.11.1), Vβ13 (MR.12.4), Vβ14 (14/2) and Vβ17 (KJ.23.288.1) specific mAb. Fixation of these mAb was revealed with FITC-conjugated F(ab)'2 goat anti-mouse Ig (Caltag) and then CD8$^+$ T cells were labeled with phycoerythrin-conjugated rat anti-mouse CD8 mAb. Human HLA-B0702 phenotyping was performed on Ficoll (Pharmacia) purified PBL by indirect immunofluorescence as indicated above using ME.1 anti-HLA-B7 antibody.

Human CTL In Vitro Restimulation and Cytolytic Assays.

Blood samples were obtained following written informed consent from platelet healthy donors tested serologically negative for HIV, HCV and HBV viruses Nitrogen-frozen HLA-B0702+Ficoll-purified human peripheral blood mononuclear cells (PBMC) were thawed and incubated (4×10$^6$/ well) in 24 well-plates in RPMI 1640, 1 mM sodium pyruvate, 100 IU/ml penicillin, 100 μg/ml streptomycin, 10 mM hepes and non-essential amino acids (all from GibcoBRL, Paisley, UK) supplemented with 10% human serum (Institut Jacques Boy, Reims, France). They were stimulated with influenza-derived peptides at 2×10$^{-6}$ M. On day 3 recombinant human IL7 (25 ng/ml, kindly provided by Sanofi-Synthelabo, Labège, France) was added and on day 7, human IL2 was added at 10 IU/ml (Roche, Mannheim, Germany) with fresh medium. On day 16, CD8$^+$ T cells were selected using CD8 Microbeads (Miltenyi Biotec, Bergish Gladbach, Germany). CTL lines were subsequently restimulated twice monthly using peptide-pulsed EBV-transformed y-irradiated (50 Gy) autologous cells. Cytolytic assays were done on $^{51}$Cr-labeled peptide-pulsed HLA-B*0702-transfected TAP$^-$ T2 cells. Specific lysis was calculated as follow: (experimental–spontaneous release)/(total–spontaneous release)×100 subtracting the background lysis (which never exceeded 5%) of HLA-B0702-restricted, HIV1-derived, GP41 (843-851) IPRRIRQGL (SEQ ID NO:42) epitopic peptide-pulsed target cells (10).

Results

Results are shown hereinafter in Tables 1 and 2.

TABLE 1

Epitopic peptides derived from HIV proteins, presented by the molecule HLA-B7 of class I and inducing a CD8 cytotoxic cellular response (CTL) in transgenic mice B7B7K$^{d+/+}$ H-2K–/– H-2D–/–

| SEQ ID NO: | N° | Protein and epitopic peptides Name | Sequence | Fixation Test RA* | $^{51}$Cr release test** R/T | Lysis (%) |
|---|---|---|---|---|---|---|
| | | | 1. Canonic peptides | | | |
| | | | GAG | | | |
| 1 | 6342 | Y10LF | YPLASLRSLF | 3.25 | 1/6 | 37 |
| | | | ENV | | | |
| 2 | 6337 | A10VV | APTKAKRRVV | 1.14 | 2/2 | 72; 58 |
| 3 | 6339 | R10LL | RPVVSTQLLL | 2.25 | 2/4 | 53; 50 |

TABLE 1-continued

Epitopic peptides derived from HIV proteins, presented by the molecule HLA-B7 of class I and inducing a CD8 cytotoxic cellular response (CTL) in transgenic mice B7B7K H-2K−/− H-2D−/−

| SEQ ID NO: | N° | Protein and epitopic peptides Name | Sequence | Fixation Test RA* | $^{51}$Cr release test** R/T | Lysis (%) |
|---|---|---|---|---|---|---|
| | | | VIF | | | |
| 4 | 6332 | K10KL | KPPLPSVTKL | 3.55 | 2/2 | 61; 31 |
| 5 | 7023 | I10VI | IPLGDARLVI | 2.33 | 4/6 | 37; 37; 22; 22 |
| 6 | 7024 | H10HI | HPRISSEVHI | 3.70 | 6/6 | 20; 18; 51; 31; 70; 48 |
| 7 | 7025 | S10EV | SPHPRISSEV | 1.11 | 6/6 | 18; 11; 38; 30; 49; 18 |
| 8 | 7020 | T9PL | TPKKIKPPL | 1.29 | 5/6 | 46; 24; 18; 18; 11; 6 |
| | | | TAT | | | |
| 9 | 7019 | P10QV | PPQGSQTHQV | 8.97 | 2/3 | 20; 13 |
| | | | REV | | | |
| 10 | 7012 | L9RL | LPLPPLDRL | 6.13 | 3/6 | 22; 12; 14 |
| 11 | 7026 | L9TL | LPPLDRLTL | 3.51 | 4/6 | 37; 20; 56; 23 |
| | | | VPU | | | |
| 12 | 7016 | Q10AL | QPIQIAIAAL | 6.5 | 6/6 | 14; 40; 16; 15; 13; 32 |

2. Non-canonic peptides, called ARFP (alternative reading frame peptides)

| | | | POL | | | |
|---|---|---|---|---|---|---|
| 13 | 7029 | A9RL | AAISPVLRL | (15) | 1/6 | 17 |
| 14 | 7028 | S10PV | SPVLRLRPPV | 0.85 | 2/6 | 24; 46 |
| | | | ENV | | | |
| 15 | 7033 | Q10QM | QPPLYFVHQM | (49) | 2/6 | 15; 13 |
| 16 | 7034 | G10QT | GPHMPVYPQT | (22) | 1/5 | 10 |
| 17 | 7031 | M9PT | MPVYPQTPT | 0.94 | 3/6 | 17; 28; 19 |
| | | | GAG | | | |
| 18 | 7035 | Q9VF | QPRSDTHVF | 1.56 | 6/6 | 61; 38; 55; 48; 43; 33 |

*Represents the ratio, between the concentrations of the peptide tested and the reference peptide (R10V human CMV pp65 265-274), that is necessary to reach 20% of the maximal level of HLA-B*0702 molecules capable of being stabilised at the surface of T2 cells in presence of a saturant concentration of the reference peptide.
**Number of mice presenting a CTL response specific to the peptide under analysis ($^{51}$Cr release test) with respect to the total number of mice tested. The lysis percentage of these mice is given for a ratio (effector:target) of 30:1.

TABLE 2

Epitopic peptides derived from HIV proteins and preferred nucleic sequences coding the same.

SEQ ID NO:

1. Canonic peptides

GAG:

```
1. Y10LF         Y    P    L    A    S    L    R    S    L    F       1
B.-.NL43E9 *    TAT  CCT  TTA  GCT  TCC  CTC  AGA  TCA  CTC  TTT      19
```

ENV:

```
2. A10VV         A    P    T    K    A    K    R    V    V            2
BRU 7306-7335  GCA  CCC  ACC  AAG  GCA  AAG  AGA  AGA  GTG  GTG       20
3. R10LL         R    P    V    V    S    T    Q    L    L            3
BRU 6571-6600  AGG  CCA  GTA  GTA  TCA  ACT  CAA  CTG  CTG  TTG       21
```

VIF:

```
4. K10KL         K    P    P    L    P    S    V    T    K    L       4
BRU 5100-5129  AAG  CCA  CCT  TTG  CCT  AGT  GTT  ACG  AAA  CTG       22
5. I10VI         I    P    L    G    D    A    R    L    V    I       5
BRU 4791-4820  ATC  CCA  CTA  GGG  GAT  GCT  AGA  TTG  GTA  ATA       23
```

TABLE 2-continued

Epitopic peptides derived from HIV proteins and preferred nucleic sequences coding the same.

| | | | | | | | | | | | SEQ ID NO: |
|---|---|---|---|---|---|---|---|---|---|---|---|
| 6. H10HI | H | P | R | I | S | S | E | V | H | I | 6 |
| BRU 4764-4793 | CAT | CCA | AGA | ATA | AGT | TCA | GAA | GTA | CAC | ATC | 24 |
| 7. S10EV | S | P | H | P | R | I | S | S | E | V | 7 |
| BRU 4758-4787 | AGC | CCT | CAT | CCA | AGA | ATA | AGT | TCA | GAA | GTA | 25 |
| 8. T9PL | T | P | K | K | I | K | P | P | L | | 8 |
| BRU 5085-5111 | ACA | CCA | AAA | AAG | ATA | AAG | CCA | CCT | TTG | | 26 |

TAT:

| | | | | | | | | | | SEQ ID NO: |
|---|---|---|---|---|---|---|---|---|---|---|
| 9. P10QV | P | P | Q | G | S | Q | T | H | Q | V | 9 |
| BRU 5583-5612 | CCT | CCT | CAA | GGC | AGT | CAG | ACT | CAT | CAA | GTT | 27 |

REV:

| | | | | | | | | | |
|---|---|---|---|---|---|---|---|---|---|
| 10. L9RL | L | P | L | P | P | L | D | R | L | 10 |
| B.US.WEAU160 | CTT | CCT | CTA | CCA | CCG | CTT | GAT | CGA | CTT | 28 |
| 11. L9TL | L | P | P | L | D | R | L | T | L | 11 |
| B.US.WEAU160 | CTA | CCA | CCG | CTT | GAT | CGA | CTT | ACT | CTT | 29 |

VPU:

| | | | | | | | | | | |
|---|---|---|---|---|---|---|---|---|---|---|
| 12. Q10AL | Q | P | I | Q | I | A | I | A | A | L | 12 |
| BRU 5646-5675 | CAA | CCT | ATA | CAA | ATA | GCA | ATA | GCA | GCA | TTA | 30 |

2. Non-canonic peptides, called ARFP (alternative reading frame peptides)

POL

| | | | | | | | | | | |
|---|---|---|---|---|---|---|---|---|---|---|
| 1. A9RL | A | A | I | S | P | V | L | R | L | | 13 |
| BRU 4167-4190 | GCA | GCA | ATT | TCA | CCA | GTA | CTA | CGG | TTA | | 31 |
| 2. S10PV | S | P | V | L | R | L | R | P | P | V | 14 |
| BRU 4173-4202 | TCA | CCA | GTA | CTA | CGG | TTA | AGG | CCG | CCT | GTT | 32 |

ENV

| | | | | | | | | | | |
|---|---|---|---|---|---|---|---|---|---|---|
| 3. Q10QM | Q | P | P | L | Y | F | V | H | Q | M | 15 |
| BRU 5945-5974 | CAA | CCA | CCA | CTC | TAT | TTT | GTG | CAT | CAG | ATG | 33 |
| 4. G10QT | G | P | H | M | P | V | Y | P | Q | T | 16 |
| BRU 6008-6037 | GGG | CCA | CAC | ATG | CCT | GTG | TAC | CCA | CAG | ACC | 34 |
| 5. M9PT | M | P | V | Y | P | Q | T | P | T | | 17 |
| BRU 6017-6043 | ATG | CCT | GTG | TAC | CCA | CAG | ACC | CCA | ACC | | 35 |

GAG

| | | | | | | | | | |
|---|---|---|---|---|---|---|---|---|---|
| 6. Q9VF | Q | P | R | S | D | T | H | V | F | 18 |
| BRU 827-853 | CAG | CCC | AGA | AGT | GAT | ACC | CAT | GTT | TTC | 36 |

EXAMPLE 2

Example 2 relates to the validation of the peptides of the present invention from HIV+ patient. A first set of experiments were done by the inventors with frozen PBMCs (peripheral blood mononuclear cells) from HIV+ patients. No clear response was observed. However, these same experiments were successfully achieved with fresh blood samples from HIV+ patients. Here is a summary of the results.

Nine HIV+ HLA-B7+ patient samples were identified by serological typing. After a thirty-hours peptide stimulation, each sample was tested ex vivo for IFNγ secretion by ELISpot assay. Statistical analysis of all 9 patient samples revealed that:

i) the eighteen selected peptides, as well as the peptides described in the litterature, elicited responses
ii) response profiles are variable among peptides, both new and already known, as well as among patients;
iii) five peptides seem particularly immunogenic in vivo and will be incorporated into the polyepitopic construct;

Two individuals (one HLA-B7+ HIV− and the other HLA-B7− HIV+) were included in this example and showed no IFNγ ex vivo response following exposure to these peptides.

Fourteen peptides are thus interesting for a future polyepitopic approach. In the case of two patients, it was observed that:

i) a depletion of CD4+ cells from PBMC harvests does not modify the observed IFNγ profile,
ii) a cytolytic response can be elicited after two courses of in vitro stimulation (as tested by $^{51}$Cr release assay).

Results

Results are shown in FIGS. 1 to 6 and in Tables 3 and 4.

As it can be appreciated, FIG. 1 shows the BNC's pattern for IFNγ ELISPOT responses against HIV-1 derived epitopic (known and new "coding" peptides), and more specifically shows the mean number (duplicates) of specific spots for $4.10^5$, $2.10^5$, and $10^5$ PBMCs.

BNC HIV-1+ patient blood was ficolled and PBMCs were directly stimulated by each peptide (5 ug/ml) or by an irrelevant peptide, such as G9AT. Elispot assay was revealed 36 h later. The immunodominant HLA-B7 restricted CMV peptide (T10M) was used for control. It will be understood that the methods or techniques used in Example 2 are well known, thus there is no need to further described them.

Figure 2:
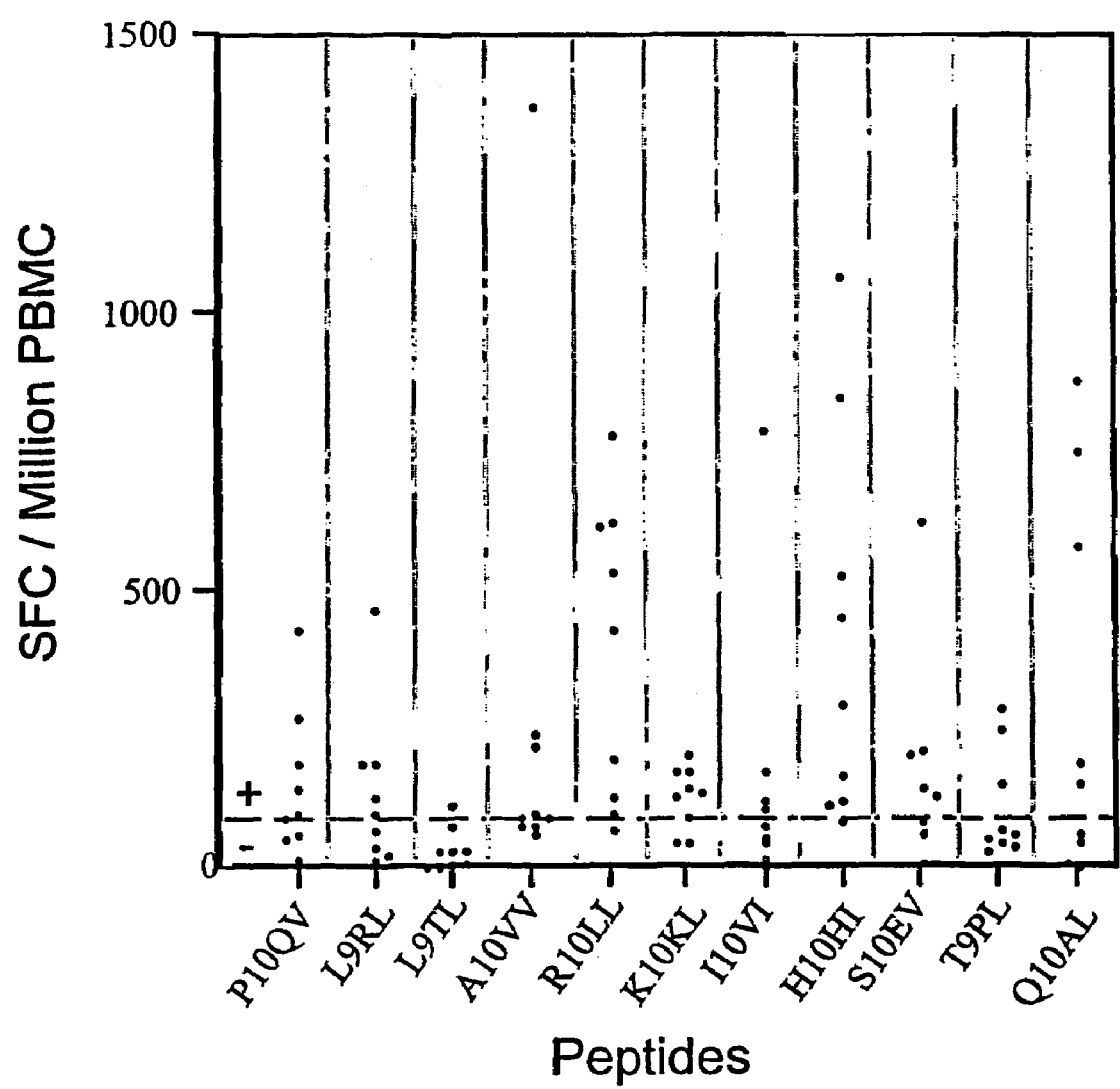
FIG. 2 shows an ELISPOT assay on human HIV+ PBMCs with <<coding>> peptides.

FIG. 2 shows the ELISPOT assay on human HIV+ PBMC (see FIG. 1 for technique). In this Figure, each spot corresponds to the number of specific spots per million of PBMCs of one HIV+ patient. 9 HIV+ patients were tested and 2 human controls were included in this study (one HIV+ HLA-B7− and the other one HIV− HLA-B7+). For each patient, ELISPOT assay response is positive in case of a the number of spots=mean of background+3 SD. Positive responses for all new "coding" peptides were observed. Nevertheless, responses for the L9TL peptide don't appear significant.

NB: CD4+ cell depletion of PBMCs has been done with 3 HIV+ patients no difference in term of ELISPOT responses was observed, implying a role of CD8+ cells in IFNγ release after peptide stimulation.

Figure 3:
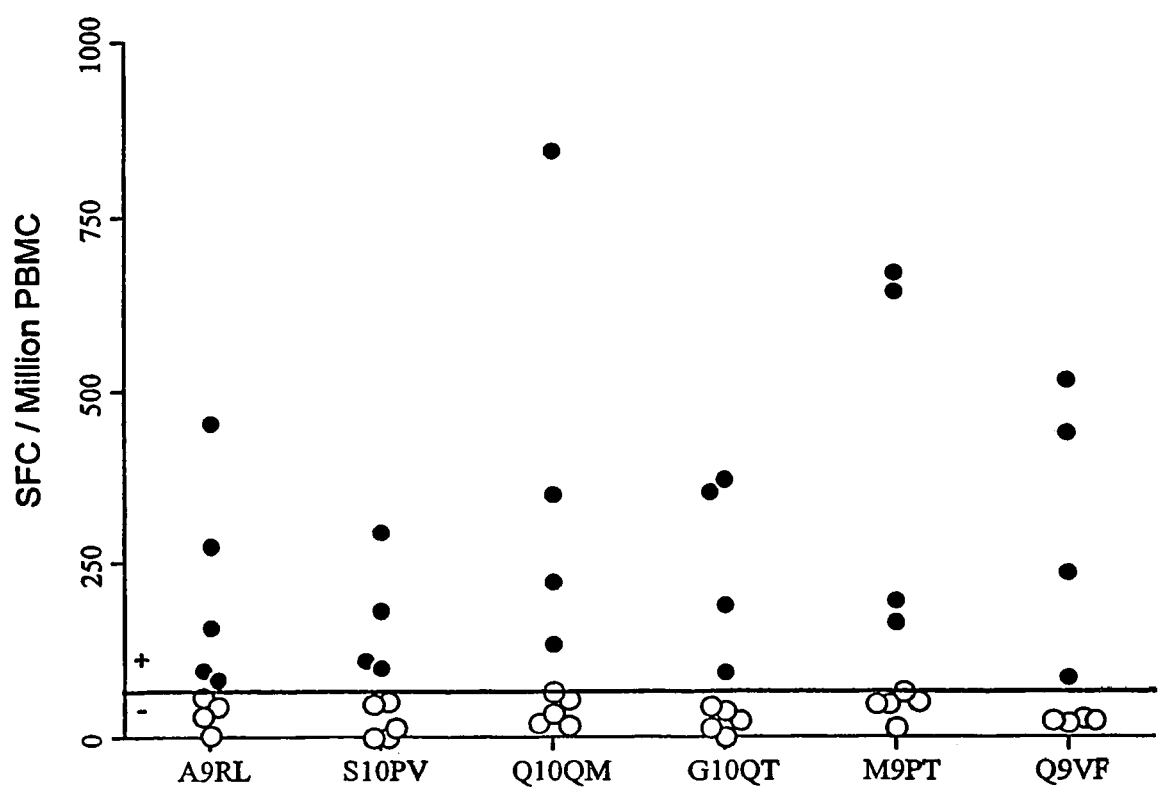
FIG. 3 shows an ELISPOT assay on human HIV+ PBMCs with the <<ARFP>> peptides.

FIG. 3 shows an ELISPOT assay on human HIV+ PBMCs with ARFP peptides (see FIGS. 1 and 2 for technique).

Among 9 HIV+ patients, positive responses were observed for all ARFP peptides. Globally, for each patient, 3 or 4 ARFP peptides are immunogenic. Despite a lower intensity of responses comparatively to "coding" peptides, it was observed that all 6 peptides are immunogenic.

Figure 4:
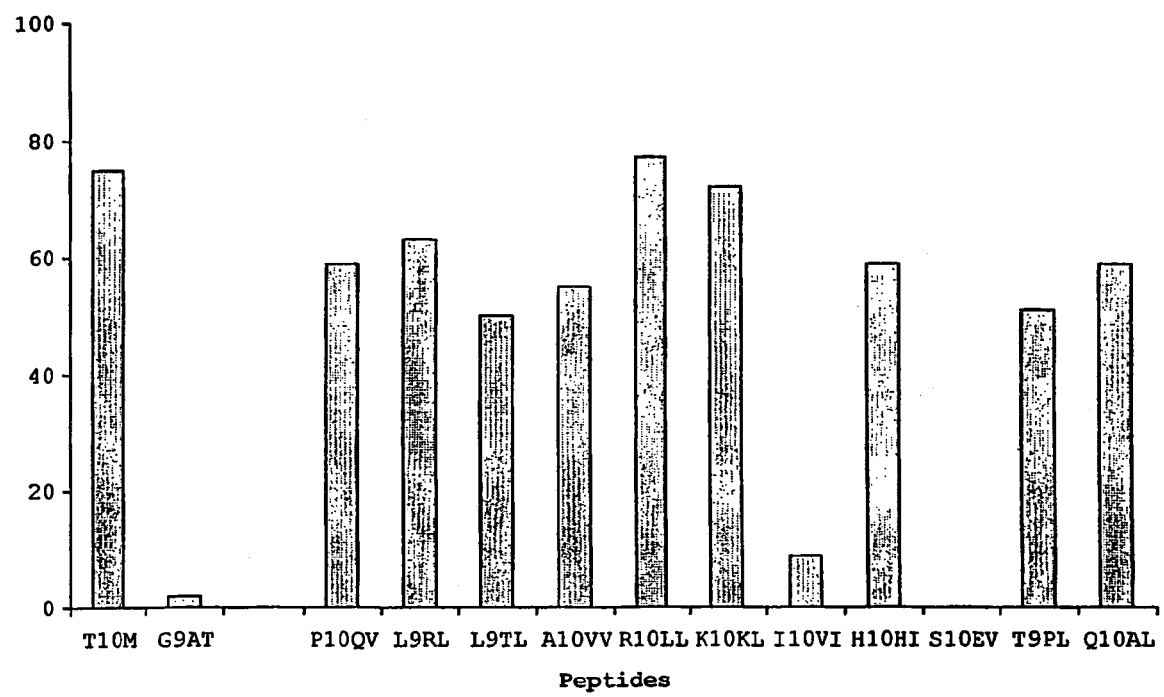
FIG. 4 is a graph showing BNC's pattern for $^{51}$Cr release assay against predicted HIV-1 derived "coding" epitopic peptides.

FIG. 4 shows the BNC's pattern for $^{51}$Cr release assay against predicted HIV-1 derived "coding" epitopic peptides. In this study, BNC HIV-1+ patient blood was ficolled and PBMCs were stimulated 2 times by peptide-pulsed autologous PHA blasts. $^{51}$Cr release assay was done on peptide-pulsed T2-B7 cells. Non specific lysis was detected by a calpaine peptide. Non HIV peptides were used as controls: T10M (CMV) and G9AT (HCV). As it can be appreciated, the $^{51}$Cr release assay in this study has confirmed results obtained by ELISPOT assay. It has been possible to do this experiment with PBMCs of an other HIV+ patient. ELISPOT responses were also confirmed by $^{51}$Cr release assay.

Figure 5:
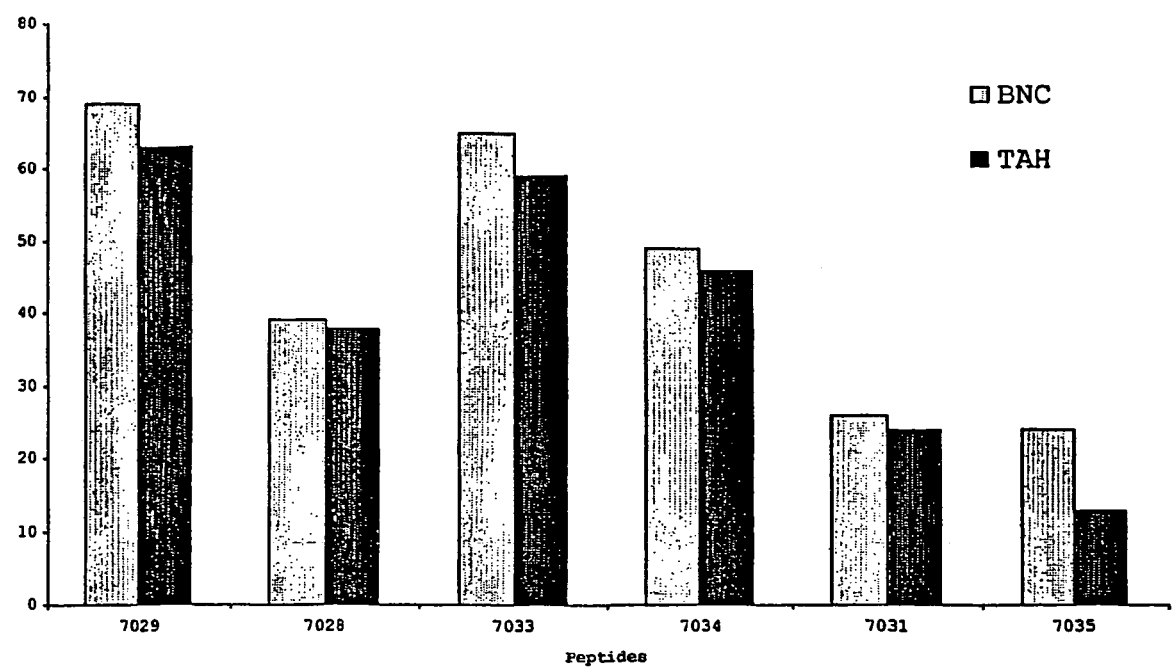
FIG. 5 is a graph showing BNC's and TAH's pattern for $^{51}$Cr release assay against predicted HIV-1 derived ARFP epitopic peptides. <<ARFP>> peptides and peptides No 5, 6, 7, 8, 9, 10, 11, are issued from the sequence of the BRU strain (Wain-Hobson et al., 1985).

FIG. 5 shows the BNC's and TAH's pattern for $^{51}$Cr release assay against predicted HIV-1 derived ARFP epitopic peptides (see FIG. 4 for technique). As it can be demonstrated in this study, patterns of $^{51}$Cr release assay responses for two HIV+ patients (BNC and TAH) were similar to those observed with ELISPOT assay. Therefore, this study shows that the 6 ARFP peptides stimulate CTL responses in human.

Figure 6A:
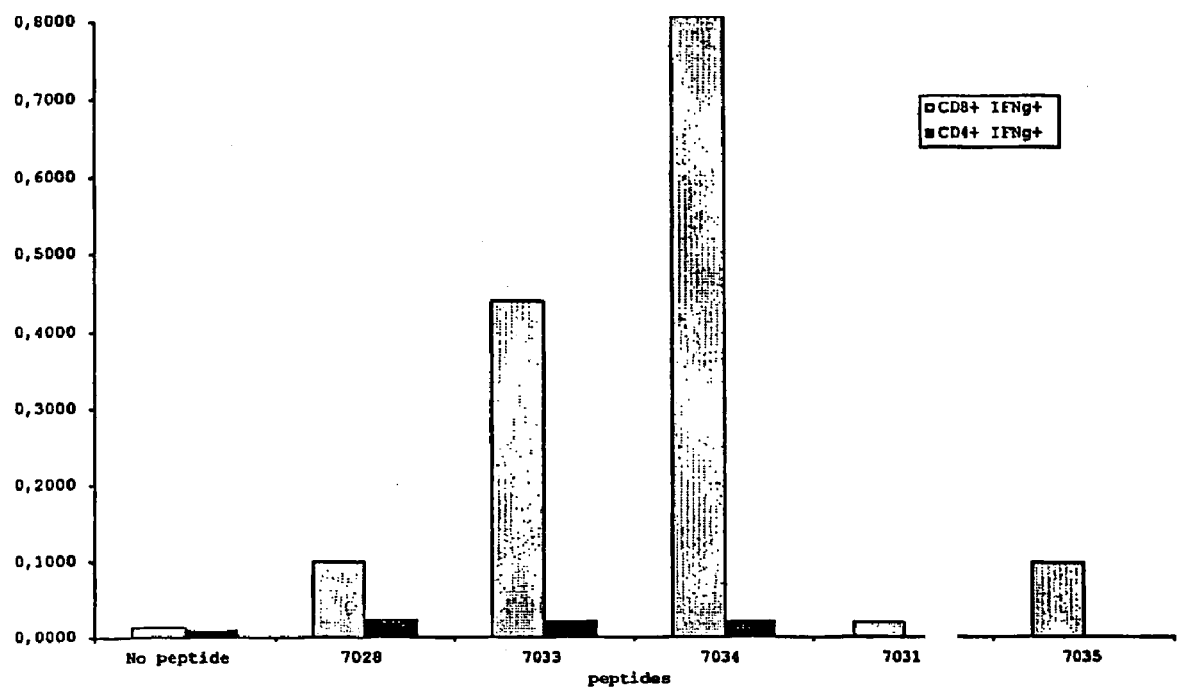
FIG. 6A shows IFNγ intracellular labeling with PBMCs of the patient TAH.

FIG. 6A shows IFNγ intracellular labeling with TAH PBMCs. In this study, TAH HIV+ PBMCs were stimulated ex vivo during 12 hours with each ARFP peptide and then, IFNγ intracellular labelling has been done. The A9RL peptide was not tested. Similarities with ELISPOT assay responses were observed. Moreover, only CD8+ cells were IFNγ labelled, excluding the possibility of a CD4+ cell stimulation by these peptides.

Figure 6B:
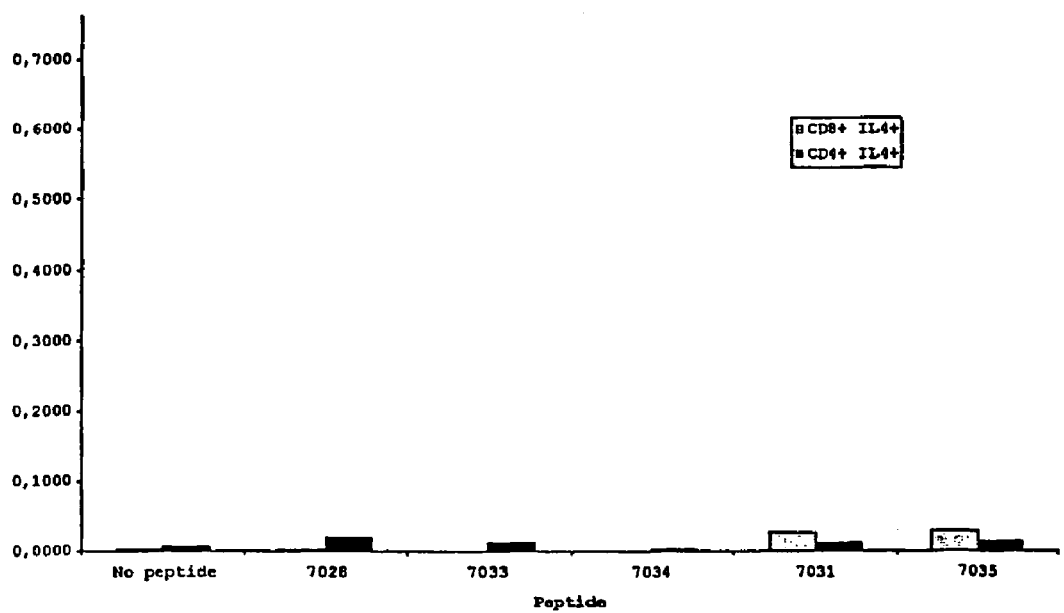
FIG. 6B shows IL4 intracellular labeling with TAH PBMCs.

FIG. 6B shows IL4 intracellular labeling with TAH PBMCs (see FIG. 6A for technique). In this study, no IL4 production was detectable after peptide stimulation, neither for CD8+ cells, nor CD4+ cells. IL4 is a cytokine produced during Th2 response. Thus, stimulation with peptides of the present invention seems inducing Th1 response, implying a stimulation of CTLs rather than helper T cells.

TABLE 3 list of "coding" HIV-1 epitopic peptides.

| SEQ ID NO: | Name | Sequence | Ref | Isolate | HXB2 location | Conservation* Clade B | All clades |
|---|---|---|---|---|---|---|---|
| 1. Known HIV-1 derived epitopic peptides | | | | | | | |
| 37 | S9WV | SPRTLNAWV | [1] | LAI | p24 (16-24) | 94% | 90% |
| 38 | T9ML | TPQDLNTML | [1] | LAI | (48-56) | 94% | 66% |
| 39 | G9VL | GPGHKARVL | [3] | SF2 B | (223-231) | 74% | 51% |
| 1 | Y10LF | YPLASLRSLF | [4] | — | pr55 (484-493) | 40% | 12% |
| 40 | K10LC | KPCVKLTPLC | [4] | — | Env (117-126) | 87% | 82% |
| 41 | R10SI | RPNNNTRKSI | [1] | LAI | gp160 (298-307) | 38% | 24% |
| 42 | I9GL | IPRRIRQGL | [1] | LAI | (843-851) | 32% | 33% |
| 43 | F10LR | FPVTPQVPLR | [1] | LAI | Nef (68-77) | 6% | 4% |
| 44 | R9AL | RPMTYKAAL | [1] | LAI | (77-85) | 6% | 4% |
| 45 | T10PL | TPGPGVRYPL | [1] | LAI | (128-137) | 17% | 16% |
| 46 | T8RY | TPGPGVRY | [5] | LAI | (128-135) | 15% | 16% |
| 47 | Y9CY | YPLTFGWCY | [5] | LAI | (135-143) | 6% | 4% |
| 48 | D10WK | DPEKEVLQWK | [4] | — | (175-184) | 6% | 4% |
| 49 | F9GL | FPRIWLHGL | [3] | SF2 B | Vpr (34-42) | 21% | 11% |
| 2. Predicted HIV-1 derived epitopic pepides | | | | | | | |
| a. Early proteins | | | | | | | |
| 9 | P10QV | PPQGSQTHQV | [6] | LAI | Tat (58-67) | 3% | 1% |
| 10 | L9RL | LPLPPLDRL | [6] | B.US.WEAU160 | Rev (73-81) | 3% | 2% |
| 11 | L9TL | LPPLDRLTL | [6] | B.US.WEAU160 | (75-83) | 3% | 2% |
| b. Structural proteins | | | | | | | |
| 2 | A10VV | APTKAKRRVV | [4] | — | gp160 (497-506) | 72% | 40% |
| 3 | R10LL | RPVVSTQLLL | [4] | — | (252-261) | 85% | 41% |
| c. Accessory proteins | | | | | | | |
| 4 | K10KL | KPPLPSVTKL | [4] | — | Vif (160-169) | 35% | 22% |
| 5 | I10VI | IPLGDARLVI | [6] | LAI | (57-66) | 26% | 17% |
| 6 | H10HI | HPRISSEVHI | [6] | LAI | (48-57) | 47% | 30% |

TABLE 3-continued list of "coding" HIV-1 epitopic peptides.

| SEQ ID NO: | Name | Sequence | Ref | Isolate | HXB2 location | Conservation* Clade B | All clades |
|---|---|---|---|---|---|---|---|
| 7 | S10EV | SPHPRISSEV | [6] | LAI | (46-55) | 5% | 3% |
| 8 | T9PL | TPKKIKPPL | [6] | LAI | (155-163) | 37% | 25% |
| 12 | Q10AL | QPIQIAIAAL | [6] | LAI | Vpu (2-12) | <1% | <1% |

*% of HIV strains presenting the same peptide amino-acid sequence (HIV databases, Los Alamos National Laboratory & National Institutes of Health, http://hiv-web.lanl.gov/cgi-bin/EPILIGN/epilign.cgi).

Comments:
1. S9WV, T9ML, R10SI, I9GL, F10LR, T10PL: C. Brander notes these are B*0702 epitopes (HIV databases 2002).
2. GPGHKARVL (SEQ ID NO: 39) was already described in HIV database 1998 ([2]). It has also been found as an immunodominant epitopic peptide ([3])
3. H10HI has been previously described as immunogenic in HIV-1 infected individuals with a less frequently sequence : HPRISSEVHI (SEQ ID NO: 6) ([3])
4. T9ML was described as an immunodominant epitopic peptide with the decamere sequence TPQDLNTML (SEQ ID NO: 38) ([4]).
5. K10LC, Y10LF and D10WK were described as subdominant peptides ([4]).
6. A10VV, R10LL, and K10KL were not described as immunogenic ([4]).

Comments:
1. S9WV, T9ML, R10SI, I9GL, F10LR, T10PL : C. Brander notes these are B*0702epitopes (HIV databases 2002).

2. GPGHKRVL (SEQ. ID. NO.: 39) was already described in HIV database 1998 ( ). It has also been found as an immunodominant epitopic peptide ( ).

3. H10HI has been previously described as immunogenic in HIV-1 infected individuals with a less frequently sequence : HPRISSEVI (SEQ. ID.NO.: 6) ( )

4. T9ML was descrtibed as an immunidominant epitopic peptide with the decamere sequence TPQDLNTML (SEQ. ID. NO.: 38) ( ).

5. K10LC, Y10LF and D10WK were described as subdominant peptides ( ).

6. A10VV, R10LL, and K10KL were not described as immunogenic ( ).

TABLE 4 list of "ARFP" new HIV-1 epitopic peptides (LAI strain)

| SEQ ID NO: | Name | Sequence |
|---|---|---|
| POL | | |
| 13 | A9RL | AAISPVLRL |
| 14 | S10PV | SPVLRLRPPV |
| ENV | | |
| 15 | Q10QM | QPPLYFVHQM |
| 16 | G10QT | GPHMPVYPQT |
| 17 | M9PT | MPVYPQTPT |
| GAG | | |
| 18 | Q9VF | QPRSDTHVF |

REFERENCES

[1] Brander C., and Goulder P. The evolving field of HIV CTL epitope mapping: new approaches to the identification of novel epitopes. HIV molecular Immunology Database: IV-1, 2001.

[2] Korber B., Brander C., Haynes C., Koup R., Moore J., and Walker B. HIV molecular Immunology Database: I-B-11, 1998.

[3] Altfeld M., Addo M. M., Eldridge R. L., Yu X. G., Thomas S., Khatri A., Strick D., Phillips M. M., Cohen G. B., Islam S. A., Kalams S. A., Brander C., Goulder P. J., Rosenberg E. S., Walker B. D., and the HIV Study Collaboration. Vpr is preferentially targeted by CTL during HIV-1 infection. J Immunol, 167(5):2743-52, September 2001.4

[4] Jin X., Roberts C. G., nixon D. F., Safrit J. T., Zhang L. Q., Huang Y. X., Bhardwaj N., Jesdale B., deGroot A. S., and Koup R. A identification of subdominant cytotoxic T lymphocyte epitopes encoded by autologous HIV type 1 sequences, using dendritic cell stimulation and computer-driven algorithm. AIDS Res Hum Retroviruses, 16(1):67-76. January 12000

[5] Lucchiari-Hartz M., van Endert P. M., Lauvau G., Maier R., Meyerhans A., Mann D., Eichmann K., and Niedermann G. Cytotoxic T lymphocyte epitopes of HIV-1 nef: generation of multiple definitive major histoccomptability complex class I ligands by proteasomes. J Exp Med, 191 (2): 239-52, Jan. 17 2000.

[6] Wain-Hobson S., Sonigo P., Danos O., Cole S., and Alizon M. Nucleotide sequence of the IADS Virus, LAV. Cell, 40:9-17, 1985.

[7] Smith, K. D. and Lutz, C. T. 1996. Peptide-dependent expression of HLA-B7 on antigen processing-deficient T2 cells. *J Immunol* 156:3755.

[8] Milich, D. R., Hughes, J. L., McLachlan, A., Thornton, G. B., and Moriarty, A. 1988. Hepatitis B synthetic immunogen comprised of nucleocapsid T-cell sites and an envelope B-cell epitope. *Proc Natl Acad Sci USA* 85:1610.

[9] Firat, H., Garcia-Pons, F., Tourdot, S., Pascolo, S., Scardino, A., Garcia, Z., Michel, M. L., Jack, R. W., Jung, G., Kosmatopoulos, K., Mateo, L., Suhrbier, A., Lemonnier, F. A., and Langlade-Demoyen, P. 1999. H-2 class I knockout, HLA-A2.1-transgenic mice: a versatile animal model for preclinical evaluation of antitumor immunotherapeutic strategies. *Eur J Immunol* 29:3112.

[10] Bette Korber, C. B., Barton Haynes, Richard Koup, John Moore, Bruce Walker Eds. 1997. HIV Molecular Immunology Database. In. Theoretical Biology and Biophysics Group, Los Alamos National Laboratory, Los Alamos, NM.

While several embodiments of the invention have been described, it will be understood that the present invention is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

We claim:

1. An isolated or purified peptide consisting of SEQ ID NO: 4, SEQ ID NO: 5, SEQ ID NO: 7, or SEQ ID NO: 8.

2. An isolated or purified immunogenic peptide according to claim 1, wherein the peptide is incorporated into a support or carrier, wherein the support is a polymer, lipidic vesicle, microsphere, latex bead, or polystyrene bead.

3. A composition comprising:
   a) at least one isolated or purified immunogenic peptide according to claim 1; and
   b) a pharmaceutically acceptable vehicle or carrier.

4. A composition comprising at least one isolated or purified immunogenic peptide according to claim 1 and human peripheral blood mononuclear cells (PBMCs).

5. A composition according to claim 4, wherein the PBMCs are HLA-B0702$^+$ cells.

6. A method for stimulating an ex vivo immune response against HIV-1 comprising:
   a) isolating from a human lymphoid or myeloid cells;
   b) incubating said cells in vitro with at least one isolated or purified immunogenic peptide according to claim 1; and
   c) allowing the induction of a cytotoxic response in vitro.

7. A method for priming human CD8$^+$ T-cells in vitro, comprising the steps of:
   a) isolating HLA-B0702$^+$ lymphoid or myeloid cells from a human patient;
   b) loading, in vitro, the cells isolated at step a) with at least one immunogenic peptide according to claim 1;
   c) isolating CD8$^+$ T-cells from said human patient; and
   d) using the cells loaded at step b) for priming, in vitro, the CD8$^+$ T-cells isolated at step c).

* * * * *

```
                           SEQUENCE LISTING

<160> NUMBER OF SEQ ID NOS: 51

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived canonic peptide

<400> SEQUENCE: 1

Tyr Pro Leu Ala Ser Leu Arg Ser Leu Phe
 1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived canonic peptide

<400> SEQUENCE: 2

Ala Pro Thr Lys Ala Lys Arg Arg Val Val
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived canonic peptide

<400> SEQUENCE: 3

Arg Pro Val Val Ser Thr Gln Leu Leu Leu
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived canonic peptide

<400> SEQUENCE: 4

Lys Pro Pro Leu Pro Ser Val Thr Lys Leu
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived canonic peptide

<400> SEQUENCE: 5

Ile Pro Leu Gly Asp Ala Arg Leu Val Ile
```

-continued

```
<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived canonic peptide

<400> SEQUENCE: 6

His Pro Arg Ile Ser Ser Glu Val His Ile
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived canonic peptide

<400> SEQUENCE: 7

Ser Pro His Pro Arg Ile Ser Ser Glu Val
 1               5                  10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      HIV-1 derived canonic peptide

<400> SEQUENCE: 8

Thr Pro Lys Lys Ile Lys Pro Pro Leu
 1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived canonic peptide

<400> SEQUENCE: 9

Pro Pro Gln Gly Ser Gln Thr His Gln Val
 1               5                  10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      HIV-1 derived canonic peptide

<400> SEQUENCE: 10

Leu Pro Leu Pro Pro Leu Asp Arg Leu
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
```

HIV-1 derived canonic peptide

<400> SEQUENCE: 11

Leu Pro Pro Leu Asp Arg Leu Thr Leu
 1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived canonic peptide

<400> SEQUENCE: 12

Gln Pro Ile Gln Ile Ala Ile Ala Ala Leu
 1               5                  10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      HIV-1 derived non-canonic peptide

<400> SEQUENCE: 13

Ala Ala Ile Ser Pro Val Leu Arg Leu
 1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived non-canonic peptide

<400> SEQUENCE: 14

Ser Pro Val Leu Arg Leu Arg Pro Pro Val
 1               5                  10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived non-canonic peptide

<400> SEQUENCE: 15

Gln Pro Pro Leu Tyr Phe Val His Gln Met
 1               5                  10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived non-canonic peptide

<400> SEQUENCE: 16

Gly Pro His Met Pro Val Tyr Pro Gln Thr
 1               5                  10

<210> SEQ ID NO 17

```
<211> LENGTH: 9
<212> TYPE: PRT
<213> ORGANISM: Artificial Sequence
<220> FEATURE:
<223> OTHER INFORMATION: Description of Artificial Sequence: Synthetic
      HIV-1 derived non-canonic peptide

<400> SEQUENCE: 17

Met Pro Val Tyr Pro Gln Thr Pro Thr
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      HIV-1 derived non-canonic peptide

<400> SEQUENCE: 18

Gln Pro Arg Ser Asp Thr His Val Phe
 1               5

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(30)

<400> SEQUENCE: 19 tat cct tta gct tcc ctc aga tca ctc ttt                           30
Tyr Pro Leu Ala Ser Leu Arg Ser Leu Phe
 1               5                  10

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(30)

<400> SEQUENCE: 20 gca ccc acc aag gca aag aga aga gtg gtg                           30
Ala Pro Thr Lys Ala Lys Arg Arg Val Val
 1               5                  10

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(30)

<400> SEQUENCE: 21 agg cca gta gta tca act caa ctg ctg ttg                           30
Arg Pro Val Val Ser Thr Gln Leu Leu Leu
 1               5                  10
```

```
<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(30)

<400> SEQUENCE: 22 aag cca cct ttg cct agt gtt acg aaa ctg                              30
Lys Pro Pro Leu Pro Ser Val Thr Lys Leu
  1               5                  10

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(30)

<400> SEQUENCE: 23 atc cca cta ggg gat gct aga ttg gta ata                              30
Ile Pro Leu Gly Asp Ala Arg Leu Val Ile
  1               5                  10

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(30)

<400> SEQUENCE: 24 cat cca aga ata agt tca gaa gta cac atc                              30
His Pro Arg Ile Ser Ser Glu Val His Ile
  1               5                  10

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(30)

<400> SEQUENCE: 25 agc cct cat cca aga ata agt tca gaa gta                              30
Ser Pro His Pro Arg Ile Ser Ser Glu Val
  1               5                  10

<210> SEQ ID NO 26
<211> LENGTH: 27
<212> TYPE: DNA
<213> ORGANISM: Artificial Sequence
<220> FEATURE:
```

```
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(27)

<400> SEQUENCE: 26 aca cca aaa aag ata aag cca cct ttg                                          27
Thr Pro Lys Lys Ile Lys Pro Pro Leu
 1               5

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(30)

<400> SEQUENCE: 27 cct cct caa ggc agt cag act cat caa gtt                                      30
Pro Pro Gln Gly Ser Gln Thr His Gln Val
 1               5                  10

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(27)

<400> SEQUENCE: 28 ctt cct cta cca ccg ctt gat cga ctt                                          27
Leu Pro Leu Pro Pro Leu Asp Arg Leu
 1               5

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(27)

<400> SEQUENCE: 29 cta cca ccg ctt gat cga ctt act ctt                                          27
Leu Pro Pro Leu Asp Arg Leu Thr Leu
 1               5

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(30)

<400> SEQUENCE: 30
```

```
caa cct ata caa ata gca ata gca gca tta                        30
Gln Pro Ile Gln Ile Ala Ile Ala Ala Leu
 1               5                  10
```

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(27)

<400> SEQUENCE: 31

```
gca gca att tca cca gta cta cgg tta                            27
Ala Ala Ile Ser Pro Val Leu Arg Leu
 1               5
```

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(30)

<400> SEQUENCE: 32

```
tca cca gta cta cgg tta agg ccg cct gtt                        30
Ser Pro Val Leu Arg Leu Arg Pro Pro Val
 1               5                  10
```

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(30)

<400> SEQUENCE: 33

```
caa cca cca ctc tat ttt gtg cat cag atg                        30
Gln Pro Pro Leu Tyr Phe Val His Gln Met
 1               5                  10
```

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(30)

<400> SEQUENCE: 34

```
ggg cca cac atg cct gtg tac cca cag acc                        30
Gly Pro His Met Pro Val Tyr Pro Gln Thr
 1               5                  10
```

<210> SEQ ID NO 35

-continued

```
<211> LENGTH: 27
<212> TYPE: DNA
<213> ORGANISM: Artificial Sequence
<220> FEATURE:
<223> OTHER INFORMATION: Description of Artificial Sequence: Synthetic
      derived HIV-1 nucleotide sequence
<220> FEATURE:
<221> NAME/KEY: CDS
<222> LOCATION: (1)..(27)

<400> SEQUENCE: 35 atg cct gtg tac cca cag acc cca acc                            27
Met Pro Val Tyr Pro Gln Thr Pro Thr
  1               5

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      HIV-1 derived nucleotide sequence
<220> FEATURE:
<221> NAME/KEY: CDS
<222> LOCATION: (1)..(27)

<400> SEQUENCE: 36 cag ccc aga agt gat acc cat gtt ttc                            27
Gln Pro Arg Ser Asp Thr His Val Phe
  1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      HIV-1 derived epitopic peptide

<400> SEQUENCE: 37

Ser Pro Arg Thr Leu Asn Ala Trp Val
  1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      HIV-1 derived epitopic peptide

<400> SEQUENCE: 38

Thr Pro Gln Asp Leu Asn Thr Met Leu
  1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      HIV-1 derived epitopic peptide

<400> SEQUENCE: 39

Gly Pro Gly His Lys Ala Arg Val Leu
  1               5

<210> SEQ ID NO 40
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      HIV-1 derived epitopic peptide

<400> SEQUENCE: 40

Lys Pro Cys Val Lys Leu Thr Pro Leu Cys
  1               5                  10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived epitopic peptide

<400> SEQUENCE: 41

Arg Pro Asn Asn Asn Thr Arg Lys Ser Ile
  1               5                  10

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      HIV-1 derived epitopic peptide

<400> SEQUENCE: 42

Ile Pro Arg Arg Ile Arg Gln Gly Leu
  1               5

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived epitopic peptide

<400> SEQUENCE: 43

Phe Pro Val Thr Pro Gln Val Pro Leu Arg
  1               5                  10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      HIV-1 derived epitopic peptide

<400> SEQUENCE: 44

Arg Pro Met Thr Tyr Lys Ala Ala Leu
  1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived epitopic peptide

<400> SEQUENCE: 45

Thr Pro Gly Pro Gly Val Arg Tyr Pro Leu
```

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      HIV-1 derived epitopic peptide

<400> SEQUENCE: 46

Thr Pro Gly Pro Gly Val Arg Tyr
 1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      HIV-1 derived epitopic peptide

<400> SEQUENCE: 47

Tyr Pro Leu Thr Phe Gly Trp Cys Tyr
 1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      HIV-1 derived epitopic peptide

<400> SEQUENCE: 48

Asp Pro Glu Lys Glu Val Leu Gln Trp Lys
 1               5                   10

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      HIV-1 derived epitopic peptide

<400> SEQUENCE: 49

Phe Pro Arg Ile Trp Leu His Gly Leu
 1               5

<210> SEQ ID NO 50
<211> LENGTH: 10
<212> TYPE: PRT
<213> ORGANISM: Homo sapiens

<400> SEQUENCE: 50

Arg Pro His Glu Arg Asn Gly Phe Thr Val
 1               5                   10

<210> SEQ ID NO 51
<211> LENGTH: 13
<212> TYPE: PRT
<213> ORGANISM: Hepatitis B virus -continued

```
<400> SEQUENCE: 51

Thr Pro Pro Ala Tyr Arg Pro Pro Asn Ala Pro Ile Leu
 1               5                  10
```